United States Patent [19]

Barberet et al.

[11] Patent Number: Plant 5,965

[45] Date of Patent: Apr. 28, 1987

[54] CARNATION NAMED LONBULOG

[75] Inventors: Nicole Barberet; Yves Ducloux, both of Antibes, France

[73] Assignee: Laboratoire de Physiologie Vegetale de la Londe, Les Maures, France

[21] Appl. No.: 669,385

[22] Filed: Nov. 8, 1984

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new variety of *Dianthus caryophyllus* particularly distinguished by the solid cardinal red coloration of its medium sized blooms which are borne on long, strong, upright stems and which bloom profusely during the recurrent blooming seasons of spring, midseason and fall, the plant having a very vigorous, upright habit with rather rigid stems and comparatively few leaves, the plant averaging about 104 cm. in height at eight months.

1 Drawing Figure

BACKGROUND OF THE NEW PLANT

This new carnation cultivar resulted as a sport of the variety "Lonsico" U.S. Plant Pat. No. 5,446 and was discovered in a cultivated area in the south of France in 1982. This sport was selected for propagation because of its considerably brighter cardinal red coloration compared with the blooms of the parent plant and propagation of this sport was first accomplished, by means of cuttings, at La Londe-Les Maures-Var, France. Continued propagation at La Londe through successive generations, both by in vitro propagation and by cuttings, at La Londe has demonstrated that the distinctive characteristics of the sport hold true from generation to generation and appear to be firmly fixed.

DESCRIPTION OF THE DRAWING

This new carnation cultivar is illustrated by the accompanying photographic drawing which shows, in full color, an arrangement of buds and flowers in various stages of opening, the colors shown being as nearly true to those specified herein as is reasonably possible to obtain by conventional photographic procedures.

DESCRIPTION OF THE NEW PLANT

The following is a detailed description of our new carnation plant based upon observations of greenhouse grown plants made at La Londe, France, in the spring of 1984, the color designations being specified according to The R.H.S. Colour Chart published by The Royal Horticultural Society of London, England.

THE PLANT

Origin: Sport.

Parentage: "Lonsico" (U.S. Plant Pat. No. 5,446).

Classification:

*Botanic.*—*Dianthus caryophyllus.*

*Commercial.*—Standard carnation.

Form: Tall, erect bush, with at least four stems being emitted near the ground.

Height: In average, about 104 cm. at eight months.

Main stem:

*Length.*—Less than 15 cm. due to pinching.

Branching character: The plant has few branches.

Growth habit: Vigorous, upright and rather rigid.

Foliage:

*Quantity.*—Moderately abundant.

*Number of leaves.*—More than 120.

*Size of leaf.*—11.5 cm. long and 1.1 cm. wide.

*Shape of leaf.*—Linear with curved margins and acute tip.

*Texture.*—Leathery.

*Color.*—Upper side — 189A/B. Under side — 189A/B.

*Ribs and veins.*—Hardly noticeable.

*Rachis.*—Hardly noticeable.

THE BUD

Form: Ovoid.

Size:

*Diameter.*—Averaging about 2.1 cm.

*Length.*—Averaging about 3.6 cm.

Opening rate: Normal.

Color of petals:

*When sepals first divide.*—Cardinal Red 53A.

*When petals begin to unfurl.*—53A.

Sepals:

*Number.*—5 to 6, joined at lower part and generally acute at the upper part. The sepals stand up when the flowers open.

*Color.*—Inside — Greenish white. Outside — 139C and 144C.

*Striae.*—Longitudinal.

Calyx:

*Size.*—Medium.

*Shape.*—Columnar.

*Splitting.*—The calyx rarely splits.

*Aspect.*—Smooth.

Flower stem:

*Length.*—About 76.5 cm.

*Color.*—189A/B.

THE FLOWER

Blooming habit: Recurrent and profuse during spring, midseason and fall, with a tendency to give few blooms in the fall.

Size of bloom: Medium.

*Diameter.*—Averaging about 8.5 cm.

*Depth.*—Averaging about 5.5 cm.

Borne: Singly.

Shape:

*When bloom first opens.*—High centered.
*When bloom matures.*—Ball-shaped.

Petalage:
*Number of petals.*—About 65 in average.
*Arrangement.*—Imbricated.
*Form.*—Of semi-circular shape and finely serrated at the apex.
*Texture.*—Soft.
*Appearance.*—Velvety.
*Color.*—All petals, upper side and reverse side, Cardinal Red 53A to 53B.

Petaloids:
*Number.*—Less than ten.
*Size.*—Smaller than the petals.
*Color.*—The same as the petals.

Flower stem:
*Length.*—About 76.5 cm.
*Character.*—Upright and of good strength.
*Color.*—189A and 189B.

Fragrance: A slight fragrance is present.

Persistence: The flowers hang on and dry.

Disease resistance: Rather tolerant to Fusarium Oxysporum as observed at Antibes, France.

Lasting quality:
*As a cut flower.*—At least ten days in vase keeping.

REPRODUCTIVE ORGANS

Stamens:

*Number.*—1 to 4.
*Arrangement.*—Around the ovary.

Anthers:
*Size.*—Less than 4 mm.
*Color.*—Greenish-white.

Filaments:
*Length.*—About 2.6 cm. in average.
*Color.*—Greenish-white.

Pistils:
*Number.*—Two.

Styles:
*Length.*—About 1.4 cm. in average.
*Color.*—White.

Stigma:
*Color.*—Lightly purplish blue.

Character of ovaries: The ovaries are ribbed.

This new carnation cultivar retains most of the physiological characteristics of the parent plant. The color of its blooms, however, is of a brilliant cardinal red with none of the purple that appears in the ruby red blooms of the parent plant.

We claim:

1. A new carnation cultivar, substantially as herein shown and described, characterized by its bright cardinal red blooms which are of medium size and are profusely produced during each of its recurrent blooming seasons.

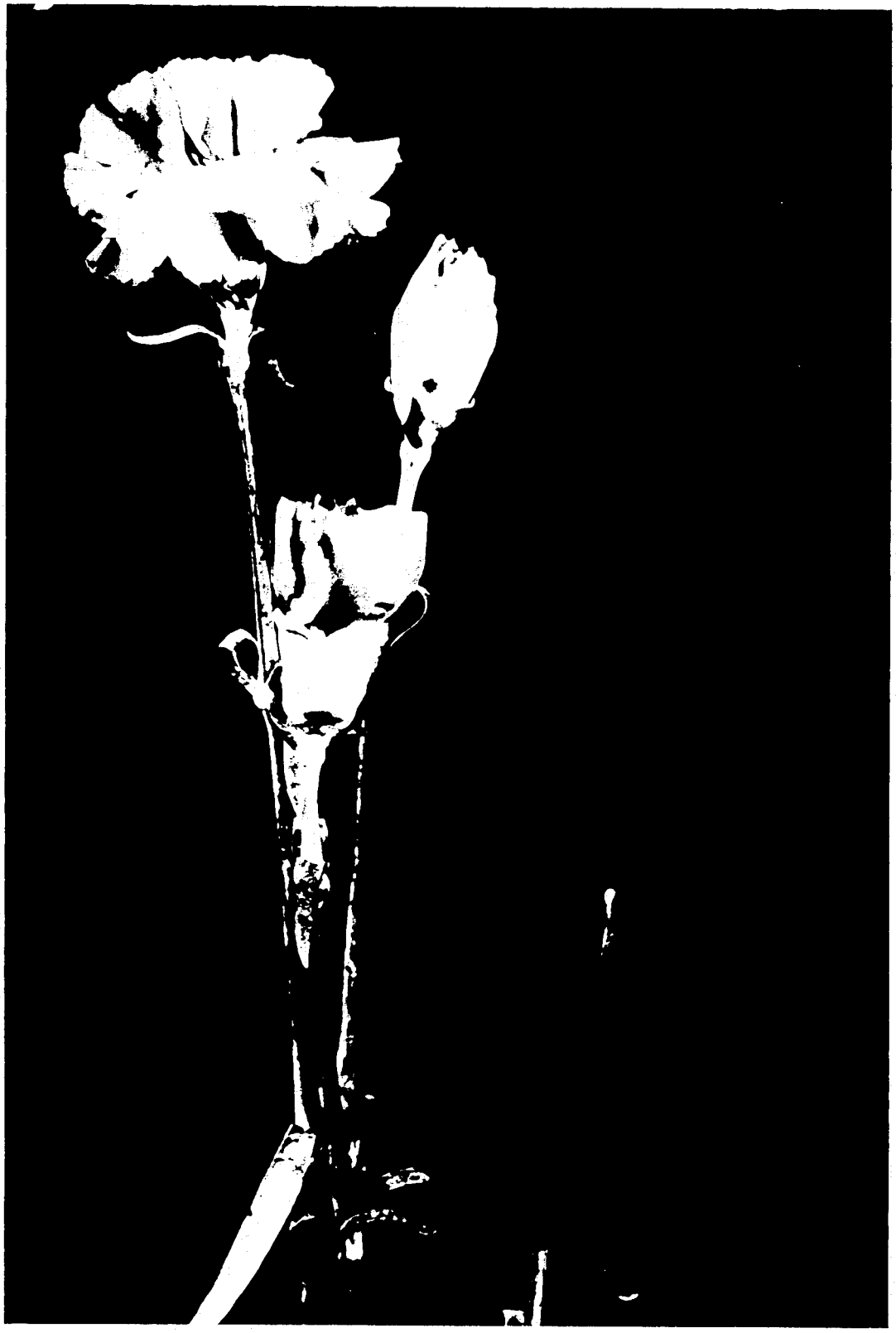

* * * * *